United States Patent [19]

Torii et al.

[11] 4,151,269
[45] Apr. 24, 1979

[54] HAIRDRESSING PREPARATION

[75] Inventors: Kenji Torii; Kenichi Tomita, both of Tokyo, Japan

[73] Assignee: Shiseido Co., Ltd., Tokyo, Japan

[21] Appl. No.: 786,540

[22] Filed: Apr. 11, 1977

[51] Int. Cl.$^2$ .............................................. A61K 7/06
[52] U.S. Cl. ........................................ 424/47; 424/70; 568/620; 568/624
[58] Field of Search .................................. 424/47, 70

[56] References Cited

U.S. PATENT DOCUMENTS

| | | | |
|---|---|---|---|
| 2,674,619 | 4/1954 | Lundsted | 560/198 |
| 3,022,335 | 2/1962 | Lundsted | 260/56 |
| 3,740,421 | 6/1973 | Schmolka | 424/70 |
| 3,830,919 | 8/1974 | Olson | 424/70 |
| 3,925,241 | 12/1975 | Schmolka | 424/70 |

*Primary Examiner*—V. D. Turner
*Attorney, Agent, or Firm*—Sughrue, Rothwell, Mion, Zinn and Macpeak

[57] ABSTRACT

A hairdressing preparation comprising at least one polyether compound resulting from the addition polymerization of 20 to 90 moles of propylene oxide to 1 mole of a polyhydric alcohol to form a main chain, and the subsequent addition polymerization of 1 to 10 moles of ethylene oxide to the resulting main chain, the amount of ethylene oxide being further within the range of 1 to 10% by weight based on the total amount of propylene oxide and ethylene oxide. The hairdressing preparation has good dressability, good feeling in use, good washability from the hair and wearing apparel and extremely low eye irritation and toxicity.

21 Claims, 2 Drawing Figures

HAIRDRESSING PREPARATION

BACKGROUND OF THE INVENTION

1. Field of the Invention

This invention relates to a hairdressing comprising at least one polyether compound resulting from the addition polymerization of propylene oxide to a polyhydric alcohol and the subsequent addition polymerization of ethylene oxide in a suitable ratio.

2. Description of the Prior Art

Base materials for hairdressings, or liquid hairdressing preparations, heretofore used include polypropylene oxide monobutyl ether (to be abbreviated hereinafter as PPBE), polypropylene oxide glyceryl ether (to be abbreviated hereinafter as PPGE), and the esters and salts thereof such as the phosphoric acid esters and K, Na, or mono-, di- or tri-ethanol amine salts of PPBE (as disclosed in Japanese Patent Publication 11955/73) and the phosphoric acid esters and K, Na, or mono-, di- or tri-ethanol amine salts of PPGE (as disclosed in Japanese Patent Publication 29141/73). These compounds, however, do not meet all of the various requirements of hairdressing bases as described below.

Nonionic PPBE and PPGE are excellent bases which have many good characteristics including high hairdressing power and good feeling in use because of their moderate oiliness, and were principal bases of early liquid hairdressings. Since they have a main chain consisting only of propylene oxide polymer, their polarities are comparatively in the oily range. Thus, they do not have any difficulties in use in water-alcohol type formulations, but after the volatilization of this solvent system, they are somewhat poor in washability from the hair, and may cause soiling of wearing apparel, etc. by infiltration of oil. Attempt has been made to remedy this defect by adding a hydrophilic ethylene oxide polymer to the propylene oxide polymer main chain. The resulting product generally has increased solubility, and the above defect is removed. However, a new disadvantage in that it has increased tendency toward whitening, swelling and other alterations of celluloid thus rendering it brittle (hereinafter for simplicity called "Celluloid alteration").

On the other hand, various phosphoric acid ester compounds of polypropylene oxide have been developed. They do have improved washability from the hair and are free from soiling of wearing apparel, but have new contradictory disadvantages. Specifically, these compounds are no longer moderately oily, but are hydrophilic with too large an increase in the number of hydrophilic polar groups present. Hence, they tend to show a deteriorated ability to retain hair setting under high humidity conditions. Furthermore, since the addition of terminal phosphate ester groups promotes intermolecular or intramolecular crosslinking, the viscosity of such a base after blending it with cosmetic ingredients is difficult to control, and the viscosity stability is poor. Thus, the dressability and feeling in use of the residue remaining after volatilization of volatile materials in the hairdressing preparation, which are important factors for liquid hairdressings, are markedly impaired. In addition, since ester compounds are anionic as a result of converting the nonionic polypropylene oxide to phosphate esters, they evidently impart increased eye irritation to animals.

SUMMARY OF THE INVENTION

An object of this invention is to provide novel and useful hairdressings which, because of moderate oiliness, have suitable dressing ability, have good affinity for the hair, have superior ability to retain hair setting, have low celluloid alteration, have good washability from the hair and good washability from wearing apparel on which it has been deposited, do not stick to the hands, and have low irritation and toxicity.

The present invention provides a hairdressing preparation comprising at least one polyether compound resulting from addition polymerization of 20 to 90 moles of propylene oxide to 1 mole of a polyhydric alcohol to form a main chain, and the subsequent addition polymerization of 1 to 10 moles of ethylene oxide to the resulting main chain, the amount of ethylene oxide being further within the range of 1 to 10% by weight based on the total amount of propylene oxide and ethylene oxide.

BRIEF DESCRIPTION OF THE ACCOMPANYING DRAWINGS

FIGS. 1 and 2 are views of hair strands used in tests to be described hereinbelow, FIG. 1 showing the hair strand before testing, and FIG. 2 showing the hair strand after testing.

DETAILED DESCRIPTION OF THE INVENTION

Figure 2:
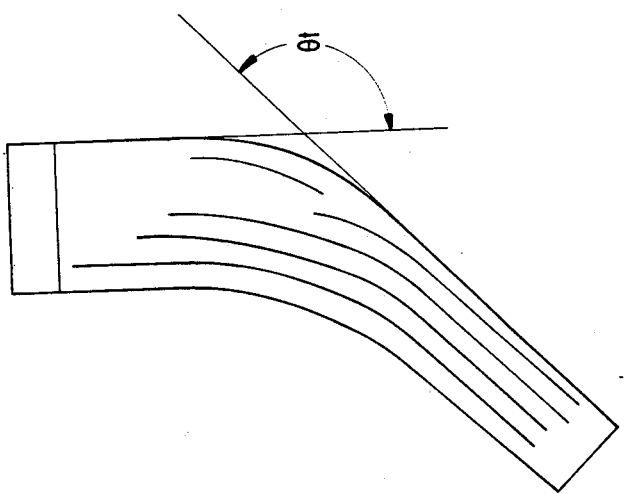
Figure 1:
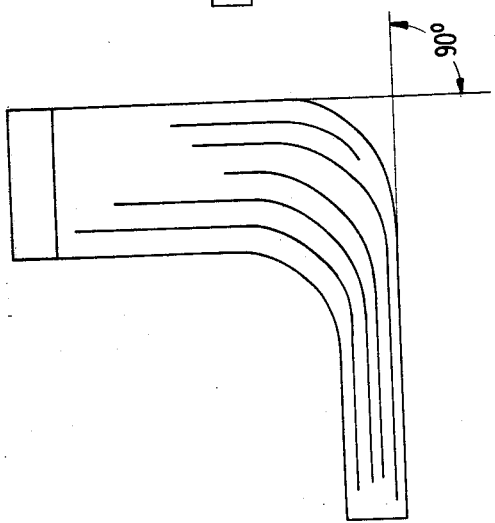

Suitable polyhydric alcohols which can be used in this invention include polyhydric alcohols containing 3 to 6 terminal hydroxyl functional groups, and the intramolecular or intermolecular dehydrocondensation products thereof. More specifically, suitable polyhydric alcohols which can be used include glycerin, pentaerythritol, trimethylol propane and trimethylol ethane, each containing therein three hydroxyl groups, and mannitol and sorbitol, each containing therein six hydroxyl groups, intramolecular dehydrocondensation products such as mannitan and sorbitan, both of which contain therein four hydroxyl groups, and intermolecular dehydrocondensation products such as diglycerin containing therein three hydroxyl groups. Of these, pentaerythritol is especially preferred.

The polyether compound is prepared by addition polymerization of 20 to 90 moles, preferably 50 to 70 moles, of propylene oxide (to be abbreviated hereinafter as PO) to one mole of this polyhydric alcohol to form a main chain, and the subsequent addition polymerization of 1 to 10 moles, preferably 3 to 7 moles, of ethylene oxide (to be abbreviated hereinafter as EO) to the main chain, the amount of ethylene oxide being further within the range of 1 to 10% by weight, preferably 3 to 7% by weight, based on the total amount of propylene oxide and ethylene oxide.

When the amount of PO of the polyether is less than 20 moles, it is insufficient for obtaining suitable dressability and ability to retain hair setting because of a low viscosity of the polyether. Amounts of more than 90 moles result in high viscosity and in an increase in molecular weight, and poor miscibility with a water/alcohol mixed solvent. Thus, hairdressings prepared from such a polyether compound have poor stability. When the amount of ethylene oxide of the polyether is less than 1 mole, washability from the hair and washability from wearing apparel are poor. If the amount of EO of the polyether is larger than 10 moles, the resulting compound results in Celluloid alteration.

On the other hand, when the amount of EO of the polyether is less than 1% by weight of the total amount of PO and EO, washability from the hair and washability from wearing apparel are poor. If the total amount is more than 10% by weight, the polyether results in Celluloid alteration.

The use of polyhydric alcohols in the present invention is for the purpose of increasing the number of terminal hydroxyl groups to which PO can be added to 3 to 6, and for increasing polarity without loss of moderate oiliness. Investigations have now shown, however, that addition polymerization of PO alone can not increase polarity to an extent which leads to a full solution of the problem of washability from the hair and from wearing apparel soiled by the hairdressing, and the addition polymerization of EO in a limited number of moles is essential.

The molecular structure of an EO-PO copolymer moiety in an adduct includes a block copolymer moiety and a random copolymer moiety. Our research work has shown that a block copolymer moiety is more water-soluble than a random copolymer moiety. Therefore, a block copolymer moiety has better washability than a random copolymer moiety and as a result the black copolymer moiety is employed in the polyether compound in this invention. The block copolymer moiety employed can be formed by first adding PO to the polyhydric alcohol in the amount indicated above and after the PO has been added, adding EO to the reaction product obtained, again in the amount indicated above, with the amounts of PO and EO being such that the ratios set forth above are achieved. Both of these copolymer moiety show the same result as regards Celluloid alteration.

Investigations were also undertaken on phosphoric acid esters of the polyether compounds used in the invention, and such have confirmed that the esters are inferior in ability to retain hair setting and usability (sticking to the hands) to the polyether compounds.

These polyether compounds can be prepared by any heretofore known manufacturing processes. For example, granular sodium hydroxide is mixed with a polyhydric alcohol in a nitrogen gas atmosphere, and PO is added slowly at a reaction temperature of about 100° to 120° C. under an internal pressure of 5 to 7 kg/cm$^2$.G. Subsequent addition of EO affords a propylene oxide/ethylene oxide addition polymer of the polyhydric alcohol. Such known methods are disclosed, for example, in U.S. Pat. Nos. 2,674,619 and 3,022,335.

The hairdressing preparation of this invention contains the polyether compound hereinabove described as a base. At least one of such a base polyether compound is dissolved in a water/alcohol solvent, and various additives required for hairdressings or heretofore used according to consumer taste can be incorporated in the solution. The alcohol used as a solvent is generally ethyl alcohol, but isopropyl alcohol can also be used. The ratio of water to alcohol is optional so long as a required amount of the base can be dissolved in the resulting mixture. Generally, the amount of the alcohol in the solvent is about 30 to about 70% by weight. The ratio of the base to the solvent is determined as desired according to whether the resulting hairdressing is in the form of a liquid, a gel, a cream, or an aerosol.

Suitable exemplary ratios of the water/alcohol solvent to the polyether base in this invention for these various hairdressing preparation forms are set forth in the table below.

Table

| Form | Water/Alcohol Solvent | Polyether Base |
|---|---|---|
| | (weight part) | (weight part) |
| Liquid | 100 | ca. 5–70 |
| Gel-like | 100 | ca. 5–50 |
| Cream-like | 100 | ca. 5–100 |
| Aerosol | 100 | ca. 40–100 |

The types and amounts of the additives used are not limited in particular. Known additives, for example, moisturizing agents (e.g., in an amount of about 0.5 to 5% by weight with examples including propylene glycol, glycerin, 1,3-butylene glycol, sodium pyrrolidone carbonate, etc.), thickeners (e.g., in an amount of about 0.1 to 2% by weight with examples including a carboxyvinyl polymer, methyl cellulose, hydroxyethyl cellulose, etc.), fungicides (e.g., in an amount of about 0.1 to 1% by weight with examples including trimethyl ammonium chloride, trichlorocarbanilide, etc.), nutritional additives (e.g., in an amount of about 0.01 to 2% by weight with examples including vitamin B$_6$, an adduct of lanolin alcohol with EO, etc.), film-forming agents (e.g., in an amount of about 0.1 to 2% by weight with examples including a pyrrolidone-vinyl alcohol copolymer, an acrylic resin, etc.), perfumes, (e.g., in a suitable amount), dyes [e.g., in a suitable amount with examples including Food, Drug & Cosmetics (to be abbreviated hereinafter as FD & C) Yellow No. 5, FD & C Blue No. 1, FD & C Red No. 2, Drug & Cosmetics (to be abbreviated hereinafter as D & C) Yellow No. 10, etc.], agents for imparting a cool feeling [e.g., in an amount of about 0.05 to 0.5% by weight with examples including l-menthol, hinokitiol ($\beta$-thujaplicin), etc.], propellants (e.g., in an amount of about 30 to 70% by weight with examples including difluorodichloromethane, tetradichloroethane etc.) and the like may be used in amounts which can achieve the purposes of addition.

The hairdressing preparation of the present invention can be manufactured by known methods.

Examples of preparing bases used in this invention and examples in which the bases were used are shown below. All parts and percentages in these examples are by weight unless otherwise specified.

The following Examples illustrate the preparation of the polyether compounds and their properties.

EXAMPLE 1

10 parts by weight of granular sodium hydroxide was mixed with 1,000 parts of pentaerythritol in a nitrogen gas atmosphere, and PO was charged into the reaction system at 95° C. to 100° C. The pressure of the reaction system was set at 5 kg/cm$^2$.G. When this pressure was reached, the feeding of PO was stopped. When the stirring of the reaction was continued, the reaction began in 1 to 2 hours, and the pressure decreased. The reaction temperature was increased to 120° C. and PO was added in a total amount of 31,500 parts, and the addition reaction was completed. After the completion of the addition reaction of PO, 1,600 parts of EO was added to the reaction system and the addition reaction of EO was conducted in the same manner as the addition reaction of PO. After completion of the reaction the product was neutralized and washed with phosphoric acid in an amount equivalent to sodium hydroxide used and dried. The thus obtained product had a viscosity of 350 centistokes at 38° C.

EXAMPLE 2

1,000 parts of EO was added to the reaction product between 1,000 parts of glycerin and 20,000 parts of PO prepared in the same way as in Example 1. The resulting product had a viscosity of 250 centistokes at 38° C.

EXAMPLE 3

950 parts of EO was added to the reaction product between 1,000 parts of sorbitol and 19,000 parts of PO prepared in the same way as in Example 1. The resulting product had a viscosity of 380 centistokes at 38° C.

Similarly, polyether compounds can be obtained using diglycerin, trimethylol propane, trimethylol ethane, mannitan, sorbitan, and mannitol.

The properties of the compounds obtained in Examples 1 to 3 are shown in Table 1.

Table 1

| Example | Polyhydric Alcohol | Moles of PO Added | Moles of EO Added | Molecular Weight | Viscosity (cst) |
|---|---|---|---|---|---|
| 1 | Pentaerythritol | 65 | 4.5 | 4,500 | 350 |
| 2 | Glycerin | 30 | 2 | 1,900 | 250 |
| 3 | Sorbitol | 60 | 4 | 4,000 | 380 |

Methods of analysis
  Moles of PO and EO: NMR spectral analysis
  Molecular weight: Calculated from the hydroxyl value
  Viscosity: Ostwald viscometer (at 38° C.)

In order to demonstrate the advantages and effects of the present invention, the various properties (i.e., solubility, washability of soiling spots deposited on wearing apparel, the ability to retain hair setting, and Celluloid alteration) of the compounds obtained in Examples 1 to 3 and conventional bases of hairdressing (PPBE, PPGE and phosphoric acid esters of these) were tested, and the results are described below.

The solubility of the polyether compounds used in the invention is high over a broad range of water/ethanol solvent systems, as is clear from Table 2 below. Thus, these polyether compounds have increased hydrophilic polarity.

Table 2

| Solvent | | Compound of Example 1 | Compound of Example 2 | Compound of Example 3 | PPBE (molecular weight, 2300) | PPGE (molecular weight, 3500) |
|---|---|---|---|---|---|---|
| Water (%) | Ethanol (%) | | | | | |
| 35 | 65 | Dissolved clear | Dissolved clear | Disslved clear | Dissolved clear | Dissolved clear |
| 50 | 50 | " | " | " | Turbid white | Turbid white |
| 65 | 35 | Turbid white | Turbid white | Turbid white | " | " |
| 75 | 25 | " | " | " | " | " |

Note:
Each compound was mixed in a concentration of 20% by weight in the solvent.

This increased polarity results in better washability of soiling spots deposited on wearing apparel, and such soiling spots can be removed completely by usual washing, as shown in Table 3 below.

Table 3

| Test Cloth | Compound of Example 1 | Compound of Example 2 | Compound of Example 3 | PPBE (molecular weight, 2300) | PPGE (molecular weight, 3500) |
|---|---|---|---|---|---|
| Woven Cloth Blend of 65% Polyester and 35% Cotton | Good | Good | Good | Poor | Poor |
| Polyester Cloth | Good | Good | Good | Poor | Poor |
| Cotton Cloth | Good | Good | Good | Poor | Poor |
| Wool Muslin | Good | Good | Good | Poor | Poor |
| Rayon Cloth | Good | Good | Good | Poor | Poor |
| Vinylon (polyvinyl alcohol) Cloth | Good | Good | Good | Poor | Poor |
| Silk Cloth | Good | Good | Good | Poor | Poor |

Note:
"Good" means that the soiling spots disappeared completely, while "Poor" means that the soiling spots remained.

The test was conducted using the following procedure.

Method of Soiling:
  50 μl of a solution of 20 parts of each of the test bases, 50 parts of ethyl alcohol and 30 parts of deionized water was coated on each of the test cloths (each having a size of 10 cm × 10 cm), and dried at room temperature (25° C.) by standing for one day.

Method of Washing:
  To 30 liters of tap water at 25° C. was added 40 g of a commercially available anionic type synthetic detergent. The soiled test cloth was placed in the resulting solution, and the solution was stirred for 10 min. in a household washer. The water was then squeezed from the cloth, the cloth rinsed for 10 min., water was then again squeezed from the cloth, and the cloth dried. The dried cloth was evaluated.

The excellent washability of the soiling spots means that in washing the hair after use of the liquid hairdressing, its removal is far easier than in the case of the conventional PPBE and PPGE.

The balance between moderate oiliness and hydrophilic polarity is an important factor which determines the function of hairdressings, such as dressability and ability to retain hair setting. The results in Table 4 below show that the polyether compounds in accordance with this invention best meet this condition.

As is clear from the results in Table 4, hairdressing containing a phosphoric acid ester of PPGE having a hydrophilic polarity increased to too large a degree has a deteriorated ability to retain hair setting under high humidity conditions. In order to retain hair setting ability, it is important to avoid moisture absorption of both the hair itself and the base compound. When the volatilization residue of a liquid hairdressing adhering to the hair has a moderate oiliness, moisture absorption of the hair is inhibited, and the ability of the hairdressing to retain hair setting is enhanced.

Table 4

| | Before Testing | 30 Minutes | 1 Hour | 2 Hours |
|---|---|---|---|---|
| Compound of Example 1 | | | | |
| Measured Value (°) | 90 | 95 | 110 | 125 |
| Retaining Ability (%) | | 94.4 | 77.3 | 61.1 |
| Compound of Example 2 | | | | |
| Measured Value (°) | 90 | 105 | 120 | 125 |
| Retaining Ability (%) | | 83.3 | 66.7 | 61.1 |
| Compound of Example 3 | | | | |
| Measured Value (°) | 90 | 100 | 115 | 130 |
| Retaining Ability (%) | | 88.8 | 72.2 | 55.6 |
| PPGE (molecular weight: 3500) | | | | |
| Measured Value (°) | 90 | 100 | 120 | 130 |
| Retaining Ability (%) | | 88.8 | 66.7 | 55.6 |
| Phosphoric Acid Ester of PPGE (molecular weight:3500) | | | | |
| Measured Value (°) | 90 | 120 | 150 | 170 |
| Retaining Ability (%) | | 66.7 | 33.3 | 11.1 |

Method of Hair Setting 5 ml of each test solution was coated on 5 g of a hair strand (15 cm long, 3 cm wide), and the solution was adhered to the hair strand uniformly with a comb. The hair strand was heat-set at an angle of 90° using a hair dryer. The hair strand was allowed to stand for one day in an atmosphere held at 25° C. and a relative humidity of 50% to dry the strand. The sample hair strand so obtained was suspended in a constant temperature-constant humidity chamber held at 25° C. and a relative humidity of 90%, and the ability to retain hair setting with absorption of moisture was measured at predetermined times.

Method of Preparing Test Solutions (1) The compounds of Preparation Examples 1 to 3 and PPGE were used in the following formulation:

| | % |
|---|---|
| Base Compound | 20 |
| Ethyl Alcohol | 50 |
| Deionized Water | 30 |

(2) The phosphoric acid ester of PPGE was used in the following formulation:

| | % |
|---|---|
| Base Compound | 20 |
| Ethyl Alcohol | 50 |
| Triethanolamine | 2.5 |
| Deionized Water | 27.5 |

The retaining ability (%) was calculated on the basis of the evaluation $$(180° - \theta t) \times \frac{10}{9}$$

so that $\theta t = 90° \ldots 100\%$ $\theta t = 180° \ldots 0\%$

Thus, the polyether compounds used in the present invention have a specific hydrophilic polarity which improves washability of soiling spots on wearing apparel and washability from the hair, and concurrently possess moderate oiliness which does not impair dressability and ability to retain hair setting.

Since the proportion of EO is limited as described hereinabove, the polyether compounds used in the present invention have reduced Celluloid alteration. This is shown in Table 5 below. A mere block polymer of PO and EO containing about 4 moles of EO swells Celluloid to an extremely high extent, but the polyether compounds in accordance with the present invention which contain a polyhydric alcohol and have a suitable polarity without increasing the chain length of EO do not cause Celluloid alteration.

Table 5

| | Base Compound Alone | 20% Solution (50% ethanol and 30% water) of the Base Compound |
|---|---|---|
| Compound of Example 1 | No change | Scarcely any change |
| Compound of Example 2 | No change | Scarcely any change |
| Compound of Example 3 | No change | Scarcely any change |
| PPGE (as described hereinabove) | No change | Scarcely any change |
| Phosphoric Acid Ester of PPGE (as described hereinabove) | No change | Scarcely any change |
| HO(EO)$_a$(PO)$_b$(EO)$_c$(*) (a + c = 4 moles; b = 30 moles) | Markedly swollen | Swollen |
| Base Compound Resulting from the Addition of 20 Moles of EO to 1 Mole of PPGE | Markedly swollen | Swollen |

(*) a and c are a number of 0 to 4.

Method of Celluloid Alteration 1 ml of each test sample was coated on a Celluloid plate (with a size of 20 cm×20 cm), and allowed to stand for one day in a constant temperature at 35° C. After washing the Celluloid plate, its surface condition was visually examined.

Furthermore, the irritation of the polyether compounds used in the present invention is about the same degree at that of the conventional PPBE and PPGE, and the compounds of this invention are superior to phosphoric acid esters of PPBE and PPGE in that their irritation to the eyelid is smaller. This is presumably because the polyether compounds used in the invention are nonionic.

Draize Method for Eye Irritation

The eyelid irritation test was performed by the Draize method using albino rabbits. The results obtained are shown in Table 6. It was found that change was observed when the test solution was instilled into the cornea and the cornea was not washed afterwards, when the phosphoric acid ester was used; whereas no change was seen in the case of using the polyether compounds in accordance with the present invention.

The Draize method used in the test was as follows;

0.1 ml of a 2% by weight aqueous solution of sodium fluorescein was applied to the corneal surface to check corneal injury 24 hours before testing.

Nine healthy albino rabbits having a body weight of 2.0 to 3.5 kg were divided into three groups. 0.003 g of each test solution was instilled into one eye of each animal. One group was retained untreated and served as a control. The eyes of other two groups were irrigated with about 20 ml of slightly warm water 2 seconds and 4 seconds, respectively, after the application of the test solution.

Plastic collars were fitted on the necks of the rabbits to prevent any unexpected reaction that might be caused by contact of the eyes with their paws.

The eyes were examined and the degrees of ocular reaction were recorded at 1 hour, 4 hours, and once a day up to 7 days.

The reactions were evaluated on the basis of evaluation scores.

Water and food were supplied ad libitum during the test period.

Table 6

| Base Compound | Evaluation | | |
|---|---|---|---|
| | Cornea | Iris | Conjunctiva |
| Compound of Example 1 | 0 | 0 | 4.7 |
| PPGE (as described hereinabove) | 0 | 0 | 4.0 |
| Phosphoric Acid Ester of PPGE (as described hereinabove) | 6.7 | 0 | 14.0 |
| Phosphoric Acid Ester of PPGE (as described hereinabove; neutralized with triethanolamine) | 0 | 0 | 8.0 |

The following formulations are examples of cosmetics in accordance with the present invention.

EXAMPLE 4

Transparent liquid hairdressing:

| | | % |
|---|---|---|
| (1) | Adduct of 1 Mole of Glycerin with 20 Moles of PO and 2 Moles of EO | 10.0 |
| (2) | Adduct of 1 Mole of Sorbitol with 60 Moles of PO and 4 Moles of EO | 8.0 |
| (3) | Propylene Glycol | 2.0 |
| (4) | Ethyl Alcohol | 40.0 |
| (5) | Perfume | suitable amount |
| (6) | FD & C Yellow No. 5 | suitable amount |
| (7) | Deionized Water | 40.0 |

(1), (2), (3) and (5) were added to (4) sequentially in this order and dissolved. (7) was added to the thus obtained solution, and then (6) was added to the solution, and the mixture was stirred. A transparent liquid hairdressing was obtained.

The hairdressing obtained had moderate dressability, had good washability from the hair, had good washability of soiling spots on wearing apparel, was not sticky, and scarcely resulted in Celluloid alteration.

EXAMPLE 5

Transparent liquid hairdressing:

| | % |
|---|---|
| Adduct of 1 Mole of Pentaerythritol with 65 Moles of PO and 4.5 Moles of EO | 50.0 |
| Glycerin | 5.0 |
| Ethyl Alcohol | 35.0 |
| Perfume | suitable amount |
| D & C Yellow No. 10] | suitable amount |
| FD & C Blue No. 1 | |
| Deionized Water | 10.0 |

The hairdressing was prepared in the same manner as in Example 4.

The resulting hairdressing had strong dressability, had great ability to retain hair setting and good washability, and was not sticky.

EXAMPLE 6

Transparent liquid hairdressing:

| | % |
|---|---|
| Adduct of 1 Mole of Diglycerin with 30 Moles of PO and 2 Moles of EO | 5.0 |
| Adduct of 1 Mole of Mannitol with 20 Moles of PO and 2 Moles of EO | 3.0 |
| Adduct of 1 Mole of Lanolin Alcohol with 5 Moles of EO | 0.5 |
| Trimethyl Ammonium Chloride | 0.1 |
| Ethyl Alcohol | 70.0 |
| l-Methanol | 0.3 |
| Vitamin $B_6$ | suitable amount |
| Perfume | suitable amount |
| FD & C Red No. 2 ⎤ FD & C Yellow No. 5 ⎦ | suitable amount |
| Deionized Water | 21.1 |

The hairdressing was prepared in the same manner as in Example 4.

The resulting hairdressing had a cool feeling, and could be used to dress the hair and set it soft while protecting the scalp.

EXAMPLE 7

Transparent liquid hairdressing:

| | % |
|---|---|
| Adduct of 1 Mole of Pentaerythritol with 90 Moles of PO and 8 Moles of EO | 7.0 |
| Adduct of 1 Mole of Sorbitan with 90 Moles of PO and 10 Moles of EO | 7.0 |
| Vinyl Pyrrolidone-Vinyl Alcohol Copolymer (Mol wt.: about 40,000) | 1.0 |
| Ethyl Alcohol | 50.0 |
| Perfume | suitable amount |
| D & C Yellow No. 10 | suitable amount |
| Deionized Water | 35.0 |

The hairdressing was prepared in the same manner as in Example 4.

The resulting hairdressing had moderate dressability, had a strong ability to retain hair setting, had good washability from the hair and good washability of soiling spots on wearing apparel, was not sticky, and scarcely resulted in Celluloid alteration.

EXAMPLE 8

Gel-like transparent hairdressing:

| | % |
|---|---|
| Adduct of 1 Mole of Trimethylol Propane with 40 Moles of PO and 5 Moles of EO | 25.0 |
| Carbopol 941 (a trademark for a carboxyvinyl polymer, manufactured by Goodrich Co., Ltd.) | 0.1 |
| Triethanolamine (used for neutralization of Carbopol 941) | 0.1 |
| Propylene Glycol | 8.0 |
| Ethyl Alcohol | 35.0 |
| Perfume | suitable amount |
| FD & C Blue No. 1 | suitable amount |
| Deionized Water | 31.8 |

The hairdressing was prepared in the same manner as in Example 4.

The resulting hairdressing had strong dressability and ability to set the hair, had good washability from the hair and good washability of soiling spots on wearing apparel, was not sticky, and scarcely resulted in Celluloid alteration.

EXAMPLE 9

Aerosol hairdressing:

| | % |
|---|---|
| Adduct of 1 Mole of Glycerin with 40 Moles of PO and 5 Moles of EO | 13.8 |
| Adduct of 1 Mole of Lanolin Alcohol with 5 Moles of EO | 0.2 |
| Propylene Glycol | 1.0 |
| Ethyl Alcohol | 10 |
| Perfume | suitable amount |
| Deionized Water | 10 |
| Difluorodichloromethane | 26 |
| Tetrafluorodichloroethane | 39 |

The above ingredients except for the difluorodichloromethane and tetrafluorodichloroethane were mixed uniformly in the same manner as in Example 4 in an aerosol container, and a valve was attached to the container. Then, the container was charged with the difluorodichloromethane and tetrafluorodichloroethane. Thus, an aerosol-type liquid hairdressing was obtained. The hairdressing had moderate dressability, had good washability from the hair and good washability of soiling spots on wearing apparel, was not sticky, and scarcely resulted in Celluloid alteration.

EXAMPLE 10

Cream-like hairdressing:

| | % |
|---|---|
| Adduct of 1 Mole of Trimethylolethane with 60 Moles of PO and 5 Moles of EO | 40 |
| Petrolatum Jelly | 5 |
| Liquid Paraffin | 3 |
| Solid Paraffin | 5 |
| Perfume | 0.2 |
| Adduct of 1 Mole of Hydrogenated Castor Oil with 40 Moles of EO | 3 |
| Adduct of 1 Mole of Stearyl Alcohol with 20 Moles of EO | 2 |
| Deionized Water | 41.8 |

The hairdressing was prepared in the same manner as in Example 4. The thus obtained hairdressing had an excellent spreading property on the hair, had a strong hair dressing property, and was not sticky.

While the present invention has been described in detail with reference to the specific embodiments thereof, it is apparent to one skilled in the art that various changes and modification can be made therein without departing the scope and the spirit of the present invention.

What is claimed is:

1. A hairdressing preparation comprising in an amount imparting good dressability, good feeling in use, good washability from the hair and wearing apparel and extremely low eye irritation and toxicity at least one polyether compound resulting from the addition polymerization of 20 to 90 moles of propylene oxide to 1 mole of polyhydric alcohol to form a main chain, and the subsequent addition polymerization of 1 to 10 moles of ethylene oxide to the resulting main chain, the amount of ethylene oxide being further within the range of 1 to 10% by weight based on the total amount of propylene oxide and ethylene oxide, said polyhydric alcohol being one or more compounds containing 3-6 functional terminal hydroxyl groups, and a solvent selected from the group consisting of water and a water-alcohol mixture in an amount sufficient to form a liquid, a gel-like, a cream-like or an aerosol preparation.

2. The hairdressing preparation of claim 1, wherein the polyhydric alcohol is a compound selected from the group consisting of glycerin, diglycerin, pentaerythritol, trimethylol propane, trimethylol ethane, mannitol, sorbitol, mannitan and sorbitan.

3. The hairdressing preparation of claim 1, wherein the polyhydric alcohol is pentaerythritol.

4. The hairdressing preparation of claim 1, wherein the amount of propylene oxide is 50 to 70 moles, and the amount of ethylene oxide is 3 to 7 moles and is also within the range of 3 to 7% by weight based on the total amount of propylene oxide and ethylene oxide.

5. A hairdressing preparation of claim 1 in a liquid form.

6. A hairdressing preparation of claim 1 in a gel-like form.

7. A hairdressing preparation of claim 1 in a cream-like form.

8. A hairdressing preparation of claim 1 in an aerosol form.

9. A hairdressing preparation which comprises a solution of the polyether compound of claim 1 in a mixed solvent of water and alcohol.

10. The hairdressing preparation of claim 1, which further contains at least one member selected from the group consisting of a dissolving or dispersing amount of an additional solvent, a moisturizing amount of a moisturizing agent, a thickening amount of a thickener, a fungicidal amount of a fungicide, a nutritional amount of a nutritional agent, a film-forming amount of a film-forming agent, a perfume odor imparting amount of a perfume, a color imparting amount of a dye, and in an amount to impart a cool feeling, an agent for imparting a cool feeling.

12. The hairdressing preparation of claim 11 wherein said moisturizing agent is selected from the group consisting of polypropylene glycol, glycerine, 1,3-butylene glycol and sodium pyrrolidone carbonate; said thickener is selected from the group consisting of a carboxyvinyl polymer, methyl cellulose and hydroxyethyl cellulose; said fungicide is selected from the group consisting of trimethyl ammonium chloride and trichlorocarbanilide; said nutritional additive is selected from the group consisting of vitamin $B_6$ and an adduct of lanolin alcohol with ethylene oxide; said film-forming agent is selected from the group consisting of a pyrrolidone-vinyl alcohol copolymer and an acrylic resin; and said agent for imparting a cool feeling is selected from the group consisting of 1-menthol and hinokitiol.

11. The hairdressing preparation of claim 10, wherein the preparation further contains up to about 5% by weight of a moisturizing agent, up to about 2% by weight of a thickener, up to about 1% by weight of a fungicide, up to about 2% by weight of a nutritional additive, up to about 2% by weight of a film-forming agent, or up to about 0.5% by weight of an agent for imparting a cool feeling.

13. The hairdressing preparation of claim 1, wherein the preparation further contains a paraffin.

14. The hairdressing preparation of claim 13, wherein the solvent is water.

15. The hairdressing preparation of claim 1, wherein the preparation further contains a propellant.

16. The hairdressing preparation of claim 15, wherein the amount of propellant is about 30 to about 70% by weight.

17. The hairdressing preparation of claim 15, wherein the solvent is a water-alcohol mixture.

18. The hairdressing preparation of claim 1, wherein the polyether is present in an amount of about 5 to about 100 parts by weight per 100 parts by weight of the water-alcohol.

19. The hairdressing preparation of claim 18, wherein the amount of alcohol in the mixture is about 30 to about 70% by weight.

20. The hairdressing preparation of claim 1, wherein the polyhydric alcohol has 3 to 6 carbon atoms.

21. The hairdressing preparation of claim 1, wherein said polyhydric alcohol is an intramolecular or intermolecular dehydration product of a polyhydric alcohol or polyhydric alcohols containing 3 to 6 terminal hyroxyl functional groups.

* * * * *